United States Patent [19]

Tock

[11] Patent Number: 5,713,901
[45] Date of Patent: Feb. 3, 1998

[54] RETICULATED ORTHOPAEDIC ELEMENT TO EXPLOIT THE MEDULLARY CANAL OF THE LONG BONES

[76] Inventor: Gideon Raphael Tock, No. 21, Via del Piscarello, 00036 Palestrina - RM, Italy

[21] Appl. No.: 586,839

[22] PCT Filed: Mar. 9, 1994

[86] PCT No.: PCT/IT94/00021

§ 371 Date: Apr. 15, 1996

§ 102(e) Date: Apr. 15, 1996

[87] PCT Pub. No.: WO95/03746

PCT Pub. Date: Feb. 9, 1995

[30] Foreign Application Priority Data

Jul. 30, 1993 [IT] Italy ............... RM93A0513

[51] Int. Cl.⁶ ............................... A61B 17/56
[52] U.S. Cl. .................. 606/62; 606/64; 606/76; 606/151
[58] Field of Search .................. 606/62, 76, 77, 606/151, 64; 623/19, 20

[56] References Cited

U.S. PATENT DOCUMENTS

| | | | |
|---|---|---|---|
| 3,662,405 | 5/1972 | Bortz et al. | 606/76 |
| 3,852,831 | 12/1974 | Dee | 623/20 |
| 3,868,730 | 3/1975 | Kaufer et al. | 623/20 |
| 3,893,196 | 7/1975 | Hochman | 606/76 |
| 3,905,777 | 9/1975 | Lacroix | 606/76 |
| 3,906,550 | 9/1975 | Rostoker et al. | 606/76 |
| 3,986,212 | 10/1976 | Sauer | 606/76 |
| 4,016,874 | 4/1977 | Maffei et al. | |
| 4,045,825 | 9/1977 | Stroot | 623/19 |
| 4,064,567 | 12/1977 | Burstein et al. | |
| 4,089,071 | 5/1978 | Kalnberz et al. | |
| 4,156,943 | 6/1979 | Collier | 606/76 |
| 4,640,271 | 2/1987 | Lower | |
| 4,820,305 | 4/1989 | Harms et al. | 623/16 |
| 4,990,161 | 2/1991 | Kampner | 623/20 |
| 5,057,110 | 10/1991 | Kranz et al. | 606/62 |
| 5,169,597 | 12/1992 | Davidson et al. | 606/76 |
| 5,397,365 | 3/1995 | Trentacosta | 606/76 |

FOREIGN PATENT DOCUMENTS

| | | |
|---|---|---|
| 0268115 | 5/1988 | European Pat. Off. . |
| 0526682 | 2/1993 | European Pat. Off. . |
| 1648421 | 6/1991 | U.S.S.R. ............... 606/76 |
| 2024631 | 1/1980 | United Kingdom . |
| 2198356 | 6/1988 | United Kingdom . |

*Primary Examiner*—Michael Buiz
*Assistant Examiner*—Julian W. Woo
*Attorney, Agent, or Firm*—Samuels, Gauthier, Stevens & Reppert

[57] ABSTRACT

Element for osteosynthesis including a central part or stem and two end parts. The two end parts have a proximal end and a distal end. The two end parts are comprised of a reticulate of titanium or other biocompatible material which is used to exploit the medullary canal of the bones. The proximal end may be temporarily coupled to an introduction instrument. The meshes of the reticulate allow for screwing of at least one transverse screw.

20 Claims, 7 Drawing Sheets

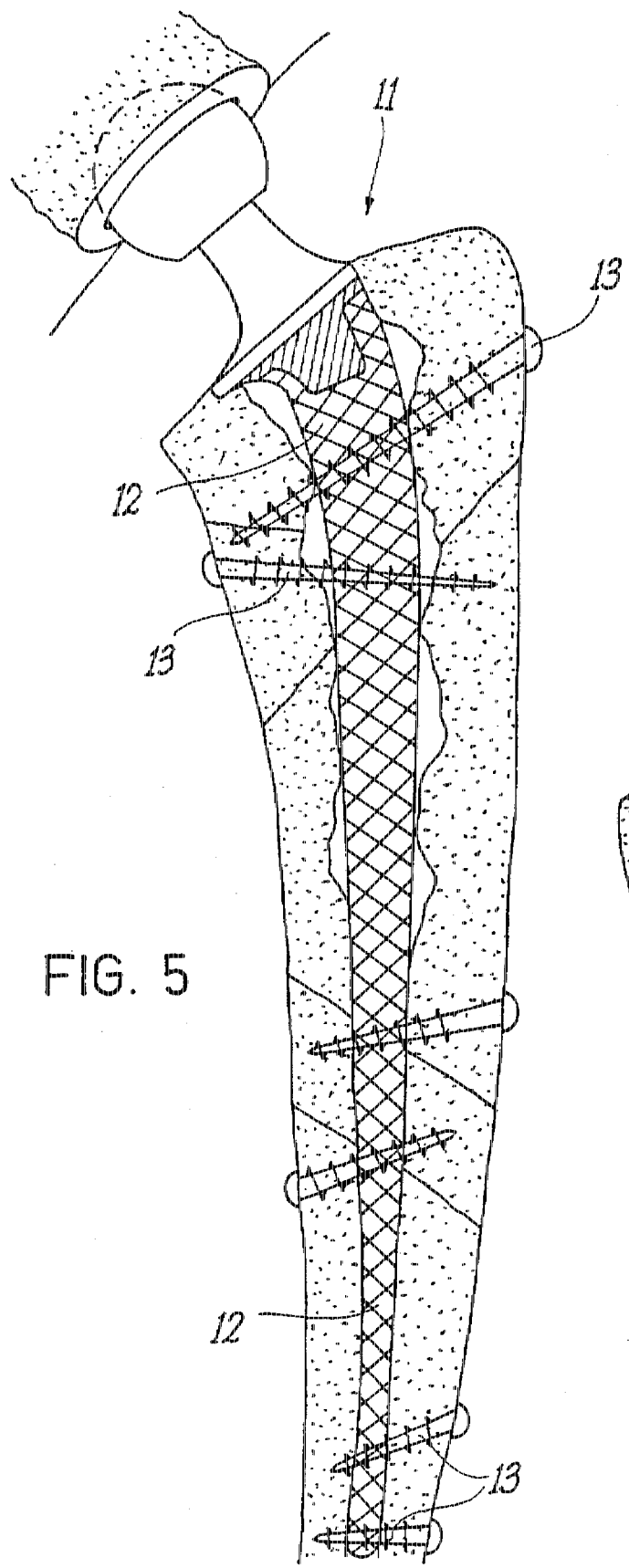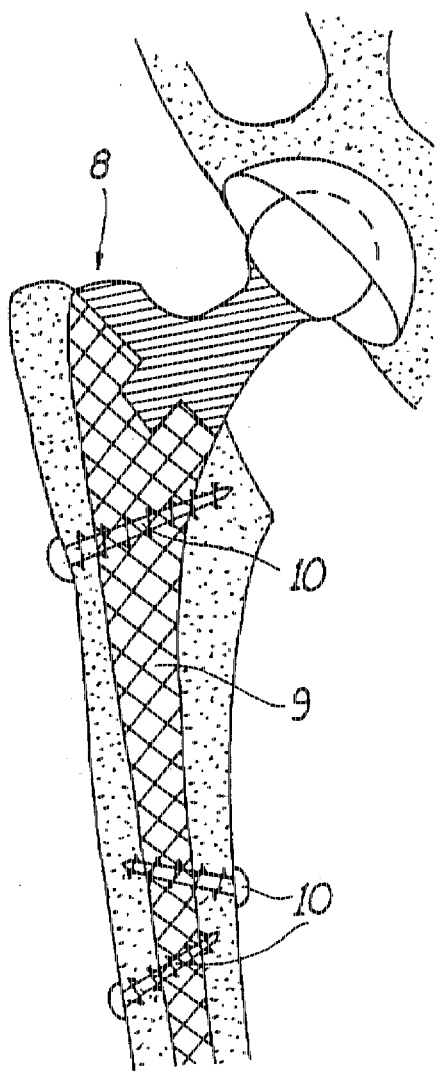
FIG. 4
FIG. 5

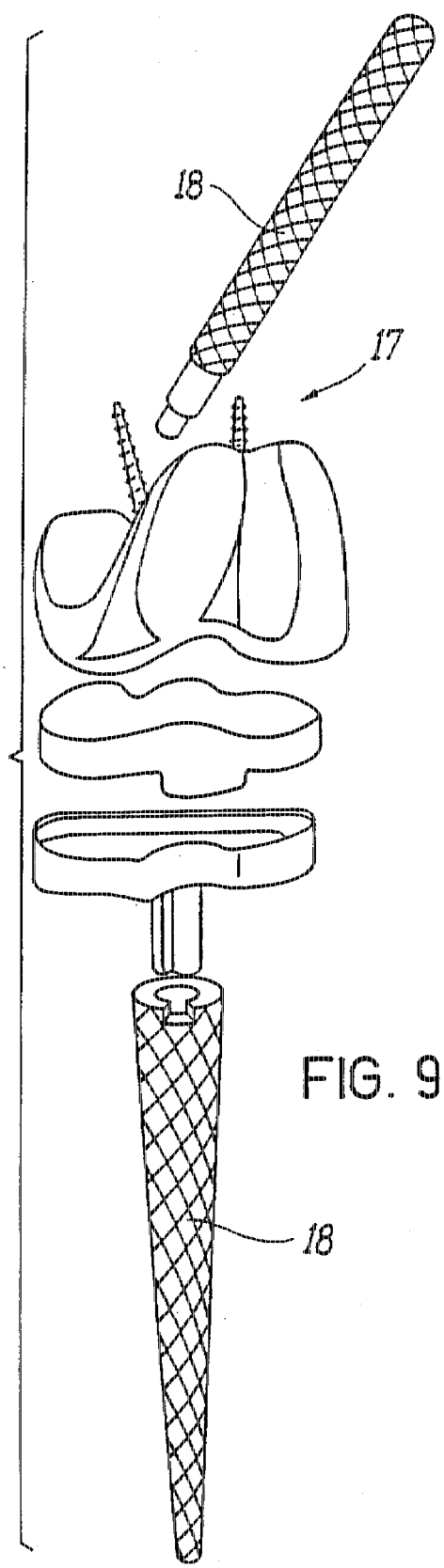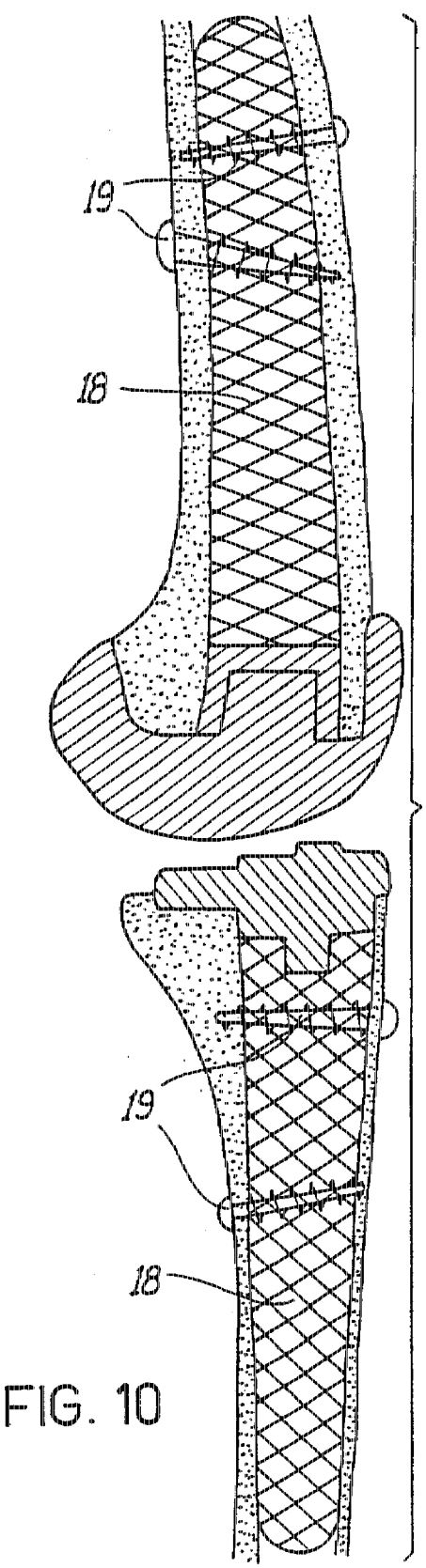
FIG. 9
FIG. 10

RETICULATED ORTHOPAEDIC ELEMENT TO EXPLOIT THE MEDULLARY CANAL OF THE LONG BONES

BACKGROUND OF THE INVENTION

1. Field of the Invention

The present invention relates to reticulated orthopaedic elements to exploit the medullary canal of the long bones.

More particularly, the invention concerns an element of the above mentioned kind, totally or partially reticulate, that, in order to be applied and transversely blocked, allows to operate without employing ray apparatuses.

As it is well known, every bone is modelled, as far as shape and mass are concerned, to satisfy to the particular mechanical necessity for the specific situation in the skeleton.

At the skeleton functional level, the bones satisfy the static and locomotion necessity. With respect to the shape, bones are divided into categories, e.g. long bones, bones having a mainly cylindrical extension with respect to the diameter, flat bones and short bones.

The long bones have an extended body, called diaphysis, and have two terminal ends, more or less broadened, called epiphysis. The long bones at the diaphysial level, if seen along a sagittal section, or by a radiographic examination, have a long and large lumen called medullary canal, surrounded by an osseous compact casing. At the epiphysial level the long bone has spongy osseous zones.

Objects of the present invention include that of finding a new application technique for the reparation and rehabilitation of traumas of long bones and of articulations, exploiting the medullary canal as bearing and support either of the prosthetic manufacture for the reparation and of the arthro-prosthetic manufacture.

2. Description of the Prior Art

At present, the orthopaedic prostheses can be classified as a) endoprostheses, arthro-prostheses (hip joint, knee, elbow, humero-shoulder prostheses, etc.): where to replace one or both of the articulation heads is replaced with a metal prosthesis; b) revision endoprostheses arthro-prostheses (hip joint, knee, elbow, humero-shoulder prostheses, etc.): wherein the second or subsequent intervention after the failure of the preceding prosthesis, only one or both of the articulation heads is replaced with a metal prosthesis.

There are also the trauma prostheses for long bones used to obtain the endomedullary osteosynthesis.

In the prostheses for the articulations, the prosthetic stem is introduced by friction within the lumen of the medullary canal to obtain a immediate primary stability.

Often, lacking this primary stability, an "orthopaedic cement" is used in order to compensate the lacking of precision in the coupling between the prosthetic stem and the medullary lumen: in this way an immediate stability is obtained, but afterwards great problems for the osseous resorption are present: in some cases even the loss of the prosthetic manufacture can occur.

The osteosynthesis technique provides the union of two or more fractured bone segments by metallic parts.

An endomedullary nail is defined as the osteosynthesis element exploiting the endomedullary lumen of the long bones. It is indicated as a locked nail, an endomedullary nail crossed by transverse or diagonal screws in correspondence of its distal and proximal ends.

EP-A-0268115 describes an element for osteosynthesis made up of a reticulate of titanium or other biocompatible material.

At present, all the endomedullary nail requires for the distal locking is the use of the image intensifier and/or other apparatuses irradiating ionizing rays during their application.

The main drawback that the present invention aims to solve is that of avoiding the necessity of using the above apparatuses to transversely introduce and lock the above-mentioned implants.

SUMMARY OF THE INVENTION

Particularly, the innovative solution according to the invention consists in the exploitation of the bearing and the support of the arthro-prosthesis, of the revision arthro-prosthesis or of the endomedullary nail, of the endomedullary lumen by a reticulate metallic structure made up by titanium or another biocompatible material that assumes the shape and the total or partial length of the medullary lumen.

The tubular reticulate shape allows to obtain a transverse anchoring in each point chosen by the operator to apply a transverse screw/clip/wire without the necessity of any control by an irradiant diagnostic apparatuses.

Simply, using the suitable mill a hole is realized. The mill in each spatial position will center a mesh of the reticulate and will allow to screw the transverse screw.

With all of the systems now available there is an unavoidable necessity use the ray apparatus. The surgeon must find the preholed seat on the prosthetic manufacture by the image of the intensifier and then mill in the corresponding point through the bone to realize the transverse locking.

As it is well known, the simple endomedullary nail alone cannot guarantee the control of rotations and cannot maintain the length of the bone in case of metaphyseal fractures and in case of plurifragmentary fractures. The traditional locked nail solves both the situations, but it is absolutely necessary to introduce and lock it to use the image intensifier.

On the contrary, an endomedullary nail realized according to the technical teachings according to the invention permits one to immobilize the complex diaphysial fractures transverse locked in every suitable position without the use of a ray and in a simple and sure way.

A reticulated endomedullary nail realized according to the invention allows the stabilization from static into dynamic, is able to promote the axial stresses on the focus thanks to the load, thus obtaining an optimum stiffening.

The solution proposed according to the present invention yields a wide possibilities of applications for the treatment of the fractures of the long bones since it can be produced with every length and diameter that varies with the varying of the different ratios medullary lumen/osseous diameter in the various anatomical zones (femur, shinbone, humerus, radium, cubitus, etc.).

The solution according to the invention enables one to make the treatment of the subtrochanteric fractures, of the fractures of the tertius distal, of the multiple, spiroidol and segmental fractures, of the comminuted fractures, of the fractures involving the loss of the osseous substance, of the pathologic fractures, of the pseudarthrosis, of the defective consolidations, of the elongation and shortening osteotomias, of the osteosynthesis in closed air.

Still according to the invention, it is possible to transform all the endomedullary nails and the primal arthroprosthesis and/or revision endomedullary stems in reticulate stems, increasing the contact surface prosthesis-bone so that a better primary and secondary coupling are obtained.

Further, according to the invention, a special advantage is obtained by eliminating the orthopaedic cement.

A further advantage is that of having the opportunity of obtaining a manufacture remarkably lighter than the prosthetic manufacture already available. The reticulate in the distal or proximal ends permits the most suitable transverse/diagonal/sagittal/oblique locking without the necessity of using a specific instrument or irradiating diagnostic apparatuses and thus guaranteeing to the patient a better primary and secondary stability.

It is therefore a specific object of the present invention that a reticulate orthopaedic element characterized in that it is comprised of a central part or stem and of two ends parts, namely a proximal end, a distal end part, in that at least said two end, pads are made up of a reticulate of titanium or other biocompatible material, in that it is used to exploit the medullary canal of the bones, in that the proximal end is provided with coupling means, for temporary coupling with an introduction instrument, and in that the meshes of the reticulate allow the screwing of at least a transverse screw.

Particularly, according to the invention, said element can be completely reticulate.

Still according to the invention, the element is made up as a unique piece, or by separated connectable parts.

In case the element according to the invention is made up of connectable parts, the connections are realized by male-female threads and/or welds, or other kind of fixed joints.

In order to allow the easy removal from the patient of the element according to the invention, said reticulate parts can be covered with a sheath made up of biocompatible plastics, e.g. Teflon®, (tetrafluoroethylene (TFE)) polyethylene, or a biocompatible thin lamina. In this case, the transverse locking is to be considered indispensable to increase the stability of the element.

Obviously, the dimensions, the thickness, the diameter and the meshes of the reticulation vary in function of the specific application, of the kind of operation and of the patient.

Further, according to the invention, particularly in case of the realization of endomedullary nails, said prosthesis will be realized innerly hollow, and provided with longitudinal grooves along all or part of the extension of the prosthesis. The grooves increase the elasticity and the flexibility of the element according to the invention, making easier both the insertion and the removal of the same.

In a preferred embodiment of the reticulate element according to the invention, it is realized in three parts, the central one being non-reticulate and having variable length and diameter, and the end ones being reticulate, standardized, and connectable with each kind of central part employed.

Further, according to the invention, the proximal end of the reticulate can be provided with male or female mechanical coupling means, for the temporary coupling with the introduction instrument.

When a prosthesis for the collum femoris is realized, the stem part of the prosthesis that is introduced within the medullary canal of the diaphysis is made up of a very strong reticulated part that allows to absorb the stem, to increase the contact surface for the osteosynthesis, and to have the opportunity of transverse blocking, this opportunity not existing with the prior art solutions.

The reticulate according to the invention will preferably have a thickness in the range between 0.05 mm and 7.0 mm.

Further, it can be made with a closely-woven weft, an open weft, or with a crossed weft.

The elements according to the invention can have any tridimensional shape which is desired, e.g. undulated, pressed, with a loosen mesh, electrowelded, with a square or rectangular mesh, S-shaped, V-shaped, O-shaped, with a right or left spiral mesh, with a plate bent at an angle between 5° and 90°, with an expanded metal, etc.

The wire constituting the reticulate can have any shape, also if observed in section.

BRIEF DESCRIPTION OF THE DRAWINGS

The present invention will be now described, in an illustrative and not limitative way, according to its preferred embodiments, with particular reference to the figures of the enclosed drawings, wherein:

FIG. 4 is a diagrammatic view of a hip joint prosthesis according to the invention;

FIG. 5 is a diagrammatic view of a revision hip joint prosthesis according to the invention;

FIG. 9 is a diagrammatic view of a revision knee prosthesis according to the invention;

FIG. 10 shows the prosthesis of FIG. 9 in place;

Figure 1:
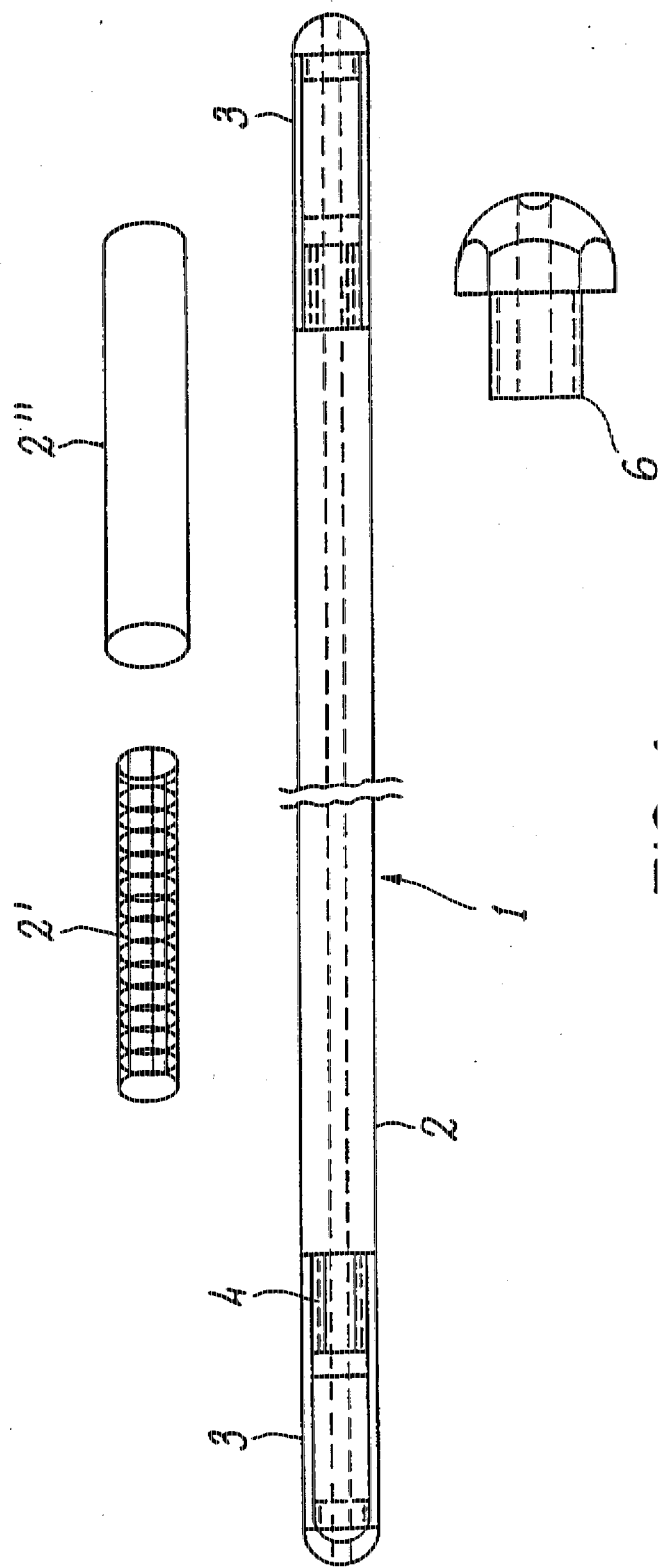
FIG. 1 shows a preferred embodiment of an endomedullary nail according to the invention.

The nail 1 of FIG. 1 has a central stem 2 and two end parts 3.

Being an endomedullary prosthesis, both the stem 2 and the end parts 3 will be centrally hollow.

Figure 2:
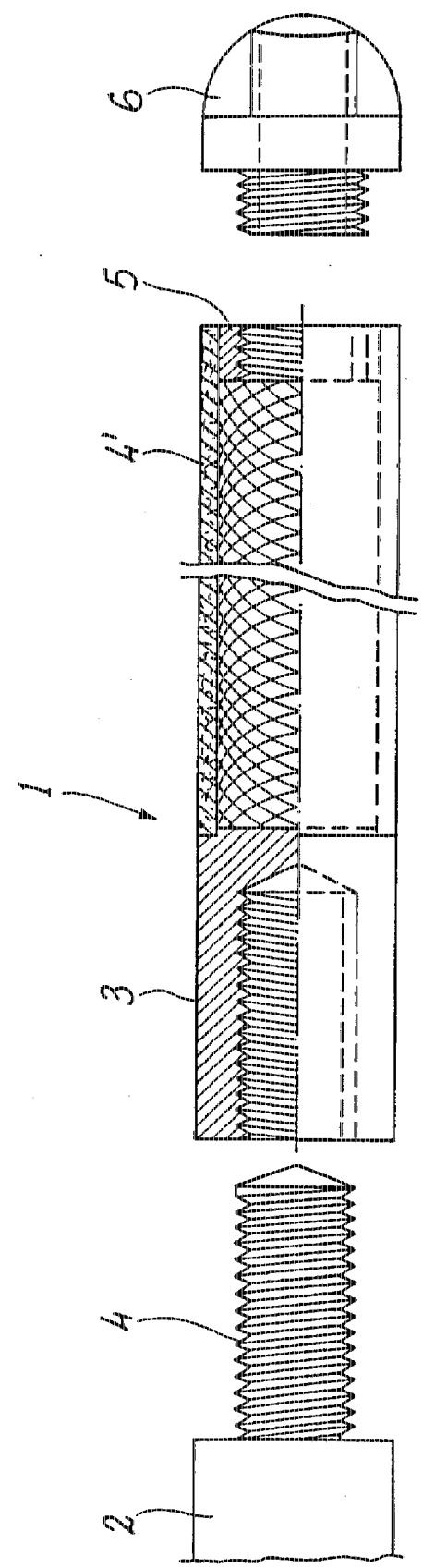
FIG. 2 shows a particular of the nail of FIG. 1.

The three parts 2 and 3 are coupled to each other, see particularly FIG. 2, by a thread 4, that obviously can be replaced by any other kind of standard coupling.

The two end parts 3 are realized by a titanium reticulate, even if a different suitable material can be used.

The meshes of the reticulation will obviously vary in function of the specific application of the prosthesis.

For example, in case of an adult of remarkable dimensions, it can have a stem having a diameter of 16 mm, wire of the reticulation having a diameter of 2.5 mm and meshes having a side comprised between 2 and 6 mm, while in case of a child, the stem can have a thickness of 10 mm, the wire of the mesh a thickness of 0.5 mm and the meshes a side of 2–3 mm.

As it can be particularly seen in FIG. 2, the reticulate parts 3 are covered with a sheath 4 realized with a biocompatible plastic material, that avoids the direct contact between bone and reticulate, easing the removal at the end of the treatment.

At the proximal end of the reticulate part 3 a coupling 5 is provided for a plug 6, that allows the coupling with the insertion instrument for the prosthesis, or with centering or measuring instruments.

Figure 3:
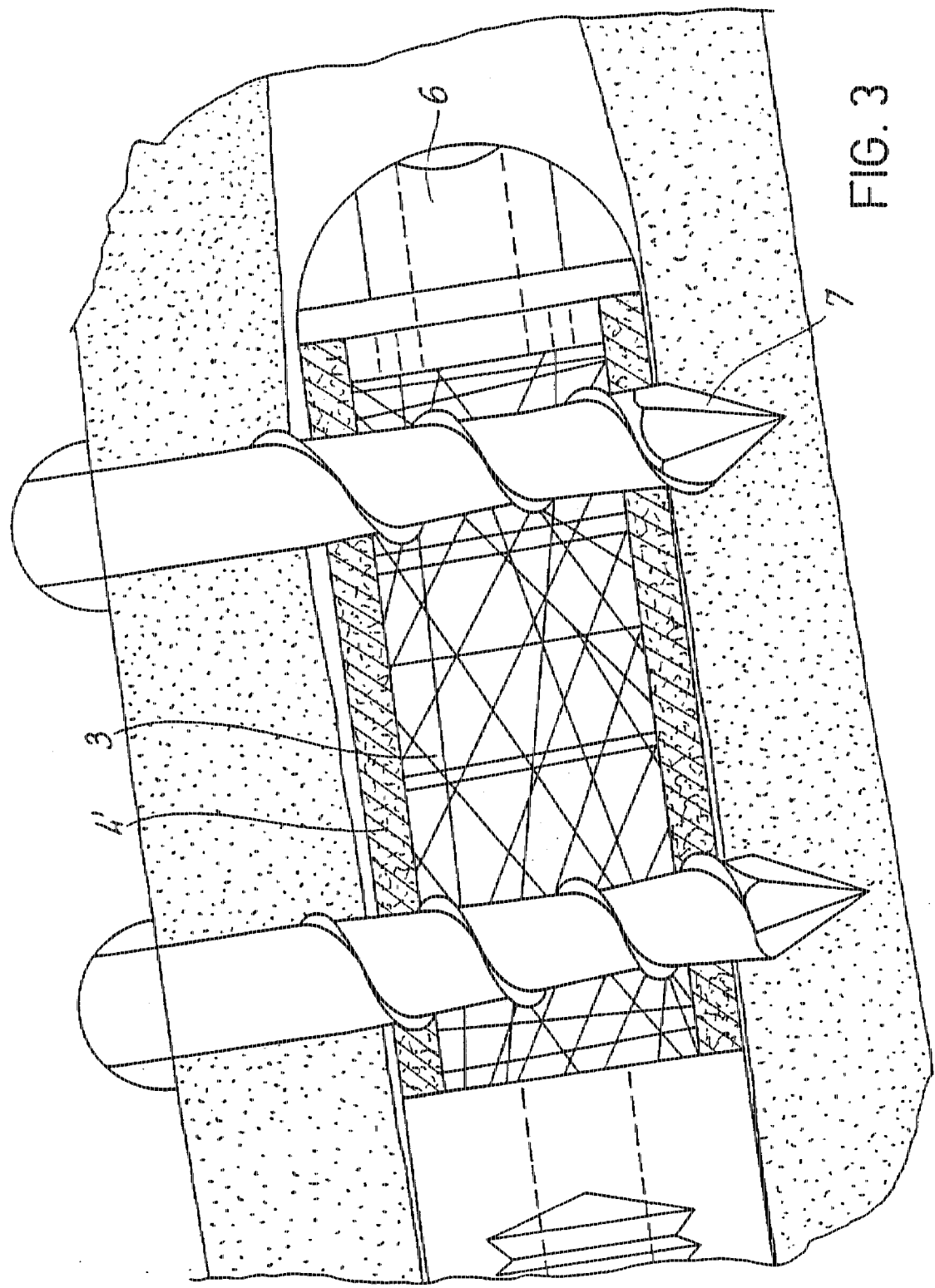
FIG. 3 shows the application of the nail according to FIGS. 1 and 2.

Coming now to observe the FIG. 3, the application of the transverse self-threading screws 7 that are introduced through the reticulate part 3, previously drilled by a mill can be observed.

The transverse locking on both the ends allows to neutralize the torsion stresses, and to maintain the same length of the segment.

Coming back to observe FIG. 1, it can be noted the global composition of the endomedullary nail realized according to the teachings of the present invention, placed within the fractured femoral medullary lumen.

The transverse locking is realized without employing the image intensifier since the orthopaedic surgeon knows that in a zone corresponding to the end parts 3 is in any case possible to realize the hole by the mill, and therefore it is sufficient that the mill centers the parts 3 to have a hole useful for the transverse locking.

Coming now to particularly see FIGS. 4 and 5, and beginning from the FIG. 4, it is shown a hip joint prosthesis 8. It has a reticulate stem 9 that allows to obtain the following advantages with respect to the already known systems:

- application of the prosthesis with the growing of the medullary bone within the medullary lumen in the reticulation of the implant stem with a remarkable increasing of the prosthetic stability, and of the osseous-implant contact surface;
- it can be avoided the use of the orthopaedic cement, and its serious drawbacks;
- it can be transversely blocked the hip joint prosthesis to the surrounding bone by the transverse fixing screws 10, without employing irradiant, diagnostic apparatuses;
- the shape and the length of the reticulate stem and the shape and the thickness of the reticulation can vary according to the specific clinical and operative necessities;
- by the cemented or not cemented prosthetic stem a primary stability of very high quality is obtained, and moreover a secondary stability having an unusual osseous-implant contact ratio is obtained.

In FIG. 5 a revision hip joint prosthesis 11 is shown: it is necessary since with the development of the clinical experience with respect to the application of the cemented or not cemented hip joint prostheses, a noticeable number of patients that after a certain period has clinical problems requiring the removal of the implant has been noticed. The lost of the implant has also the consequence that the surrounding bone is damaged and is compromised in such a way not to be more able to sustain the static/dynamic load of the patient and/or not to be more possible to be a suitable seat for the new implant. To this compensation of the loss of the surrounding bone, the invention asks the total or partial exploiting of the femoral medullary lumen applying a long stem 12 transversely locked by the transverse screws 13.

The advantages obtained are those already mentioned herein before. Moreover, a further increasing of the prosthetic stability and a structural compensation for the bone are obtained as a consequence of the lost of the implant.

Figure 6:
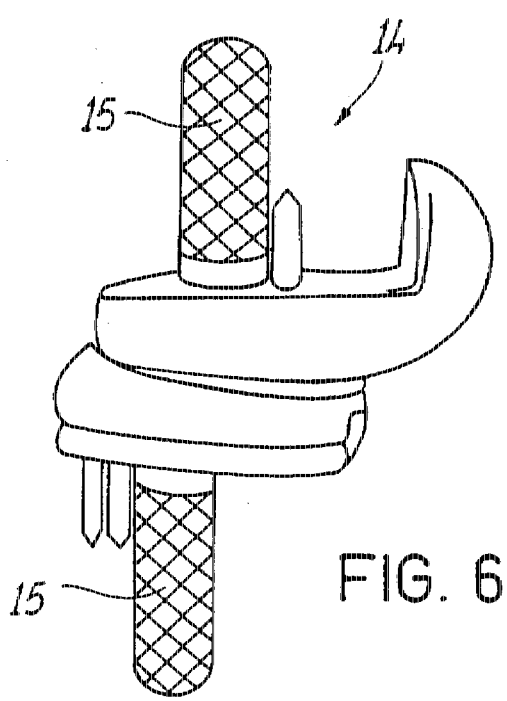
FIG. 6 is a diagrammatic view of a knee prosthesis according to the invention.
Figure 7:
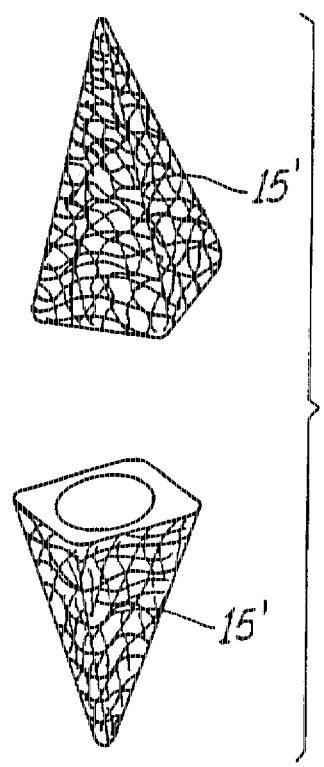
FIG. 7 diagrammatically shows a different shape of a stem for a knee prosthesis according to FIG. 6.
Figure 8:
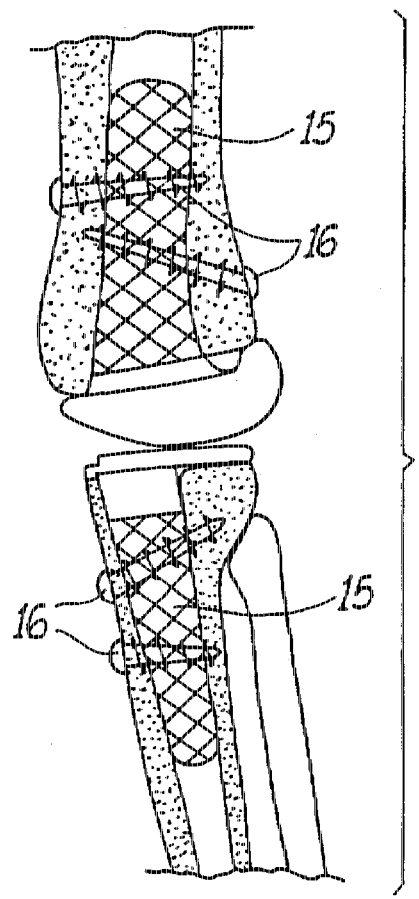
FIG. 8 shows the prosthesis of FIG. 6 in place.

Coming now to observe FIGS. 6-8, a knee joint prosthesis 14 is shown.

In the prosthetic articulation of the knee, the longitudinal vertical part that is introduced in the femoral medullary lumen and in the tibial medullary lumen is realized by a tubular reticulate cylinder 15: in this way higher primary and secondary stability are guaranteed, with the opportunity and the easy ease of transversely locking the prosthesis 14 without image intensifier by the screws 16.

In FIG. 7 a stem 15' is shown having different shape and length.

It can also be realized a revision prosthesis 17 (see FIGS. 9 and 10), introducing a reticulate tubular cylindrical stem 18 longer than the main stem so that it is possible to compensate the osseous lost and to noticeably increase the ratio between the support osseous surface and the reticulate surface of the stem, either the tibial or the femoral stem or both.

Further, since the stem is reticulate, it is possible the transverse locking of the same in every point of its extension by transverse screw 19.

Figure 11:
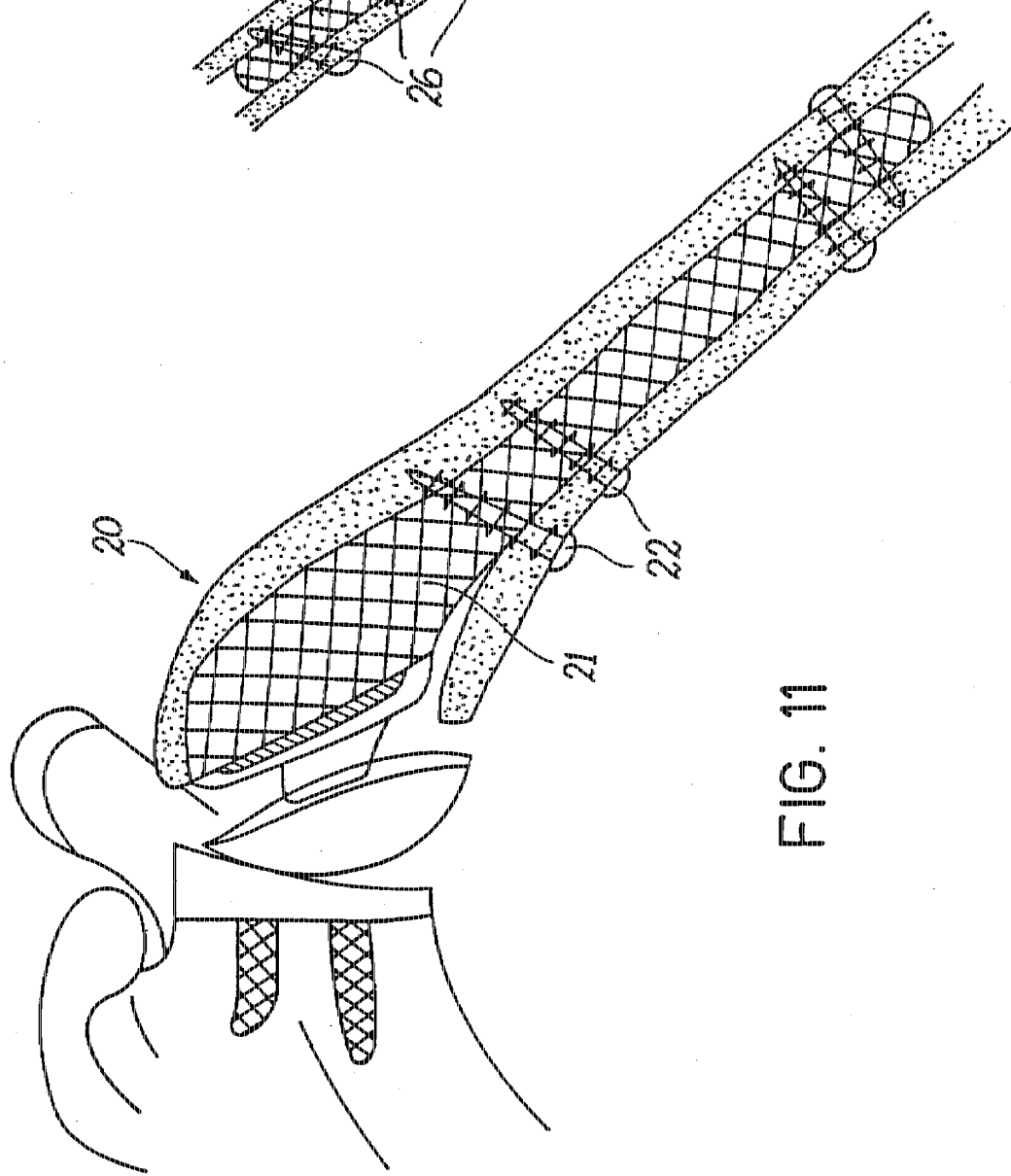
FIG. 11 is a diagrammatic view of a humero-scapular prosthesis according to the invention.

Coming now to observe FIG. 11, a humero-scapular prosthesis 20 is shown comprising a reticulate stem 21 introduced within a medullary lumen, allowing thus the transverse locking of the prosthetic manufacture by the screw 22 and further to lighten in a conclusive manner the weight of the prosthetic manufacture.

Figure 12:
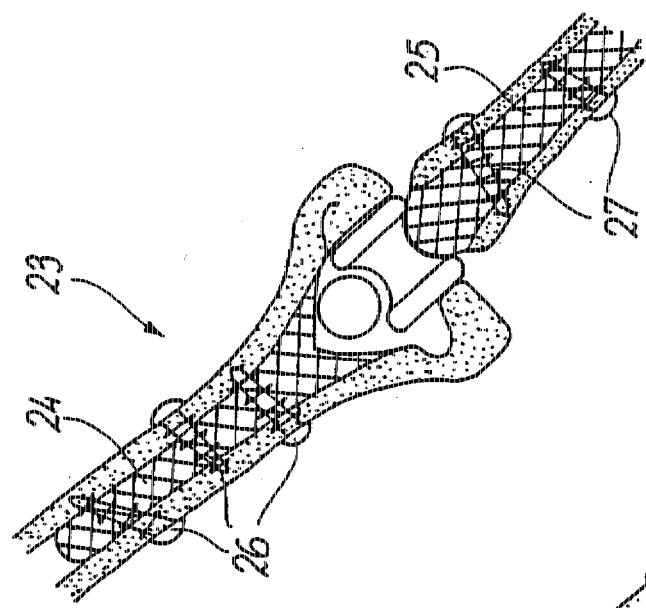
FIG. 12 is a diagrammatic view of an elbow prosthesis according to the invention.

Finally, observing FIG. 12, an elbow-humero-cubitus prosthesis 23 is shown providing a reticulate humero stem 24 and a reticulate cubitus stem 25 allowing a best performance and prosthetic stability with respect to the traction and rotation movements ahead and backward stressing the elbow articulation.

Both the stem 24 and the stem 25 are fixed by the screws 26 and 27.

The present invention has been described in an illustrative and not limitative way, according to its preferred embodiments, but it is to be understood that changes and/or modifications can be introduced by those skilled in the art without departing from the scope of the invention as defined by the enclosed claims.

I claim:

1. Element for osteosynthesis comprising a central part and two end parts, the two end parts include a proximal end and a distal end part, such that said two end parts are comprised of a reticulate of titanium or other biocompatible material which is used to exploit the medullary canal of the bones, said proximal end is provided with coupling means, for temporary coupling to an introduction instrument, and wherein the meshes of the reticulate allow the screwing of at least a transverse screw, wherein said reticulate parts are covered with a sheath of biocompatible plastics, selected from the group consisting essentially of polytetrafluoroethylene or polyethylene, or a biocompatible metal, or thin titanium lamina, such that the sheet prevents a bond between the bone tissue and screw and such that said element may be introduced into a patient without the use of an image intensifier.

2. Element for osteosynthesis according to claim 1, wherein said element is completely reticulated.

3. Element for osteosynthesis according to claim 1, wherein said element is made up as one piece.

4. Element for osteosynthesis according to claim 1, wherein said element is made of separated connectable parts.

5. Element for osteosynthesis according to claim 4, wherein said connectable parts are coupled by male-female threads, welds, or other kind of fixed joints.

6. Element for osteosynthesis according to claim 1, wherein said element is innerly hollow.

7. Element for osteosynthesis according to claim 6, wherein said element is provided with longitudinal grooves.

8. Element for osteosynthesis according to claim 1, wherein said element is comprised of three parts, the central one being non-reticulate and having variable length and thickness; the end parts being reticulate and standardized, and connectable with said central part.

9. Element for osteosynthesis according to claim 1, wherein the proximal end of the reticulate is provided with male or female mechanical coupling means for the temporary coupling to the introduction instrument.

10. Element for osteosynthesis according to claim 1, wherein the reticulate has a thickness in the range between 0.05 mm and 7.0 mm.

11. Element for osteosynthesis according to claim 1, wherein said reticulate is made with a closely-woven weft or open weft, or with a crossed weft.

12. Element for osteosynthesis according to claim 1, wherein said element is used as an endomedullary nail.

13. Element for osteosynthesis according to claim 1, wherein said element is used as a hip joint prosthesis.

14. Element for osteosynthesis according to claim 1, wherein said element is used as a revision hip joint prosthesis.

15. Element for osteosynthesis according to claim 1, wherein said element is used as a knee prosthesis.

16. Element for osteosynthesis according to claim 1, wherein said element is used as a revision knee prosthesis.

17. Element for osteosynthesis according to claim 1, wherein said element is used as a scapolo-humero prosthesis.

18. Element for osteosynthesis according to claim 1, wherein said element is used as a revision scapolo-humero prosthesis.

19. Element for osteosynthesis according to claim 1, wherein said element is used as an elbow (humero-cubitus) prosthesis.

20. Element for osteosynthesis according to claim 1, wherein said element is used as a revision elbow (humero-cubitus) prosthesis.

* * * * *